United States Patent [19]

Markel et al.

[11] Patent Number: 5,624,413
[45] Date of Patent: Apr. 29, 1997

[54] METHOD FOR INSERTING A MULTIPLE CATHETER ASSEMBLY

[75] Inventors: David F. Markel, Collegeville; Anthony J. Madison, Harleysville, both of Pa.

[73] Assignee: Medical Components, Inc., Harleysville, Pa.

[21] Appl. No.: 606,152

[22] Filed: Feb. 23, 1996

[51] Int. Cl.$^6$ .................................................. A61M 25/00
[52] U.S. Cl. .......................... 604/280; 604/43; 604/174; 604/175; 604/283
[58] Field of Search .............................. 604/43, 96, 174, 604/175, 280, 283; 606/194

[56] References Cited

U.S. PATENT DOCUMENTS

| | | |
|---|---|---|
| 390,177 | 9/1888 | Lee . |
| 701,075 | 5/1902 | McCully . |
| 3,359,974 | 12/1967 | Khalil . |
| 3,400,714 | 9/1968 | Sheridan . |
| 3,804,097 | 4/1974 | Rudie . |
| 3,823,720 | 7/1974 | Tribble . |
| 3,863,632 | 2/1975 | Schwartz . |
| 4,072,146 | 2/1978 | Howes . |
| 4,098,275 | 7/1978 | Consalvo . |
| 4,203,436 | 5/1980 | Grimsrud . |
| 4,385,631 | 5/1983 | Uthmann .............................. 604/43 X |
| 4,405,313 | 9/1983 | Sisley et al. ........................ 604/43 |
| 4,427,012 | 1/1984 | Miller . |
| 4,432,752 | 2/1984 | Marlon . |
| 4,451,252 | 5/1984 | Martin . |
| 4,493,696 | 1/1985 | Uldall ................................... 604/43 |
| 4,583,968 | 4/1986 | Mahurkar . |
| 4,682,978 | 7/1987 | Martin .................................. 604/43 |
| 4,692,141 | 9/1987 | Mahurkar . |
| 4,770,652 | 9/1988 | Mahurkar . |
| 4,808,155 | 2/1989 | Mahurkar . |
| 4,895,561 | 1/1990 | Mahurkar . |
| 4,898,669 | 2/1990 | Tesio ................................ 604/248 X |
| 5,053,023 | 10/1991 | Martin ............................... 604/280 |
| 5,084,013 | 1/1992 | Takase . |
| 5,156,592 | 10/1992 | Martin et al. ......................... 604/43 |
| 5,167,220 | 12/1992 | Brown . |
| 5,197,951 | 3/1993 | Mahurkar . |
| 5,209,723 | 5/1993 | Twardowski et al. ................ 604/43 |
| 5,334,167 | 8/1994 | Cocanower ......................... 604/280 |
| 5,336,220 | 8/1994 | Ryan et al. . |
| 5,374,245 | 12/1994 | Mahurkar . |
| 5,385,548 | 1/1995 | Williams et al. . |

FOREIGN PATENT DOCUMENTS

| | | |
|---|---|---|
| 0834211 | 2/1978 | Belgium . |
| 1092927 | 1/1981 | Canada . |
| 1285953 | 12/1962 | France . |

OTHER PUBLICATIONS

Hocken, A.G., "Percutaneous Femoral Vein Catheterization for Hemodialysis: A Single Needle Technique," *Clinical Nephrology*, vol. 12, No. 2, 1979, pp. 93–94.

Brochure entitled "The Medcomp TESIO Catheter", MEDCOMP, Harleysville, PA, date unknown, 4 pages.

B. Canaud, J.J. Beraud, H. Joyeux, C. Mion "Internal Jugular Vein Cannulation with Two Silicone Rubber Catheters" Artificial Organs 1986; 10(5):397–403.

F. Tesio et al. "Double Catheterization of the Internal Jugular Vein for Hemodialysis" Artificial Organs 1994; 18(4):301–304.

*Primary Examiner*—Sam Rimell
*Assistant Examiner*—Robert V. Racunas
*Attorney, Agent, or Firm*—Panitch Schwarze Jacobs & Nadel, P.C.

[57] ABSTRACT

A method is provided for inserting a multiple catheter assembly into an area of a body to be catheterized through a single incision. Two independent catheters which are independently movable with respect to each other, or unattached to each other, along their entire length are inserted into the single incision. In use, the first catheter withdraws fluid from the area and the second catheter delivers fluid to the area. As part of the insertion method, the longitudinal distance between proximal portions of the two catheters are adjusted to provide a predetermined longitudinal distance between distal portions of the two catheters within the area.

20 Claims, 5 Drawing Sheets

METHOD FOR INSERTING A MULTIPLE CATHETER ASSEMBLY

FIELD OF THE INVENTION

The present invention relates to a single-insertion method for inserting a multiple catheter assembly into an area within the body.

BACKGROUND OF THE INVENTION

Catheters for the introduction or removal of fluids may be located in various venous locations and cavities throughout the body for the introduction or removal of fluids. Such catheterization may be performed by using a single catheter having multiple lumens. A typical example of a multiple lumen catheter is a dual lumen catheter in which one lumen introduces fluids and one lumen removes fluids. Catheterization may also be performed by using separate, individual single lumen catheters inserted through two different incisions into an area to be catheterized. Such multiple catheter assemblies are known as Tesio catheters.

Generally, to insert any catheter in a blood vessel, the vessel is identified by aspiration with a long hollow needle in accordance with the Seldinger technique. When blood enters a syringe attached to the needle, the syringe is disconnected and a thin guide wire is passed through the needle into the interior of the vessel. The needle is then removed leaving the guide wire within the vessel. The guide wire projects beyond the surface of the skin.

At this point, several options are available to a physician for catheter placement. The simplest is to pass a catheter into the vessel directly over a guide wire. The guide wire is then removed leaving the catheter in position within the vessel. However, this technique is only possible in cases where the catheter is of a relatively small diameter, made of a stiff material and not significantly larger than the guide wire, for example, for insertion of small diameter dual lumen catheters. If the catheter to be inserted is significantly larger than the guide wire, a dilator device is first passed over the guide wire to enlarge the hole. The catheter is then passed over the guide wire, and the guide wire and dilator are removed.

In the case of an individual, single-lumen catheter useful for insertion of multiple catheter assemblies (e.g., a Tesio catheter), a physician may use an introducer sheath. If a Tesio is used for hemodialysis, for example, each catheter is inserted in two separate veins, such as the femoral vein. Alternatively, each catheter is inserted in two different locations of the same vein, such as the internal jugular vein. The introducer sheath is simply a large, stiff thin-walled tube which serves as a temporary conduit for the permanent catheter which is being placed. The introducer sheath is positioned by placing a dilator device inside of the introducer and passing both the dilator and the introducer together into the vessel. A guide wire, left in the vessel after insertion by syringe as described above, and the dilator are then removed, leaving the thin-walled introducer sheath in place. The catheter is placed through the introducer sheath. Each of the catheters in the assembly is typically subcutaneously secured within the patient's body by subcutaneous tunnellings, or is externally affixed to the body.

The Tesio double catheter assembly while comfortable for the patient and very effective for hemodialysis still requires multiple procedures and incisions, thereby increasing the attendant risk of catheterization. However, the Tesio double catheter assembly provides the ability to independently insert and remove the catheters such that dialysis need not be unnecessarily prolonged.

To avoid double tunnelling procedures for Tesios, one recent catheter design provides a connected Tesio. The individual catheters are permanently linked in one portion by a retaining sleeve and distal ends are prespaced by an appropriate distance. The retaining sleeve fits snugly around the individual catheters. The sleeve is subcutaneously positioned below the incision site and outside the area to be catheterized. The sleeve renders the assembly self-retaining such that tunnelling is optional. While this device requires only one incision, it lacks the advantage of standard Tesios which are independently removable. Furthermore, if one individual catheter becomes clogged, develops a leak, or otherwise requires replacement, the entire double catheter assembly must be removed. If the patient is undergoing dialysis, the entire process must be stopped and a time-consuming and invasive surgical procedure must be performed to remove and replace the assembly in the manner of a multiple lumen catheter.

Dual lumen catheters are inserted through a single incision procedure. However, dual lumen catheters suffer from the same disadvantages as the Tesio double catheter assembly highlighted above in that one lumen cannot be replaced independently of the other lumen. Many dual lumen catheters also have poor flow characteristics due to the shape and size of the individual lumens.

Thus, there is a need in the art for a simple method of catheterization which is requires only one procedure, which takes advantage of the benefits provided by Tesio catheters, and which does not suffer from the shortcomings of the methods highlighted above. The present invention fills such a need.

SUMMARY OF THE INVENTION

The present method provides a method for inserting a multiple catheter assembly into an area of a body to be catheterized. The assembly comprises a first and a second catheter, each catheter having a distal portion and a proximal portion. The first catheter withdraws fluid from the area. The second catheter delivers fluid to the area. The first and second catheters are independently movable with respect to each other, or unattached to each other, along their entire length. The method includes the steps of making an incision near the area, inserting the distal portions of the first and second catheters through the incision and into the area, adjusting a longitudinal distance between the proximal portions of the first and second catheters to provide a predetermined longitudinal distance between the distal portions of the first and second catheters within the area, optionally closing the incision, and securing the proximal portions of the first and second catheters.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings plural embodiments which are presently preferred. It should be understood, however, that the invention is not limited to the precise arrangements and instrumentalities shown. In the drawings, like numerals are used to indicate like elements throughout. In the drawings.

DETAILED DESCRIPTION OF THE PREFERRED EMBODIMENT

Certain terminology is used in the following description for convenience only and is not limiting. The words "right," "left," "lower" and "upper" designate directions in the drawings to which reference is made. The words "proximal" and "distal" refer to directions away from and closer to, respectively, for example, the insertion ends of the first and second catheters in a double catheter assembly according to the present invention. The terminology includes the words above specifically mentioned, derivatives thereof, and words of similar import.

Referring now to the drawings in detail, where like numerals indicate like elements throughout, there are shown in FIGS. 1 through 7, multiple catheter assemblies, generally indicated as 10 for use with a preferred method of the present invention. The catheter assemblies 10 are inserted into an area 12 of a body 14 for removing and introducing fluids to the area 12. Once the catheter assembly 10 is properly inserted and positioned in the catheterization area 12, the assembly 10 is secured to a fixed source or location in or on the body 14, such as a subcutaneous area 16 in the body 14 (shown in FIG. 3) or an external surface 18 of the body 14 (shown in FIG. 6), such as the skin.

The catheter assembly 10 can be adapted for use in various applications in which bodily fluids, medicaments or other solutions are introduced into and removed from the body such as perfusion, infusion, plasmapheresis, hemodialysis, chemotherapy, and the like. The area to be catheterized is preferably a blood vessel such as an internal jugular vein, but may be any area within the body. Other areas in which the catheter assembly 10 may be used include, for example, other blood vessels, including the femoral and subclavian veins, any abscess cavity, post-operative cavity, the peritoneal cavity, and other areas of the body including intra-abdominal, sub-diaphragmatic and sub-hepatic areas. It should be understood by one of ordinary skill in the art from this disclosure that these areas are exemplary, and that the catheter assembly 10 may be used to remove or introduce fluids in various areas to be catheterized. The preferred embodiment of the invention as shown, is preferably useful for intake, or removal, of blood to be purified from a blood vessel, such as the internal jugular vein, and introduction of purified blood into the same vessel. The blood can be purified by any suitable hemodialysis apparatus (not shown). The catheters may also be used to introduce medication or other fluids such as glucose or saline solutions into the body.

For the purposes of describing the preferred embodiment of the present invention, the device will be described with respect to the preferred application of hemodialysis, more specifically, for purifying blood flowing through the internal jugular vein 20 of a human being, near the right atrium of the heart (not shown). However, it will be understood by one skilled in the art based on this disclosure, that the assembly 10 can be configured and adapted, by increasing or decreasing the catheter size and/or number, such that the assembly 10 can be beneficially used for other medical applications in which fluids are introduced into and/or removed from the body.

Figure 1:
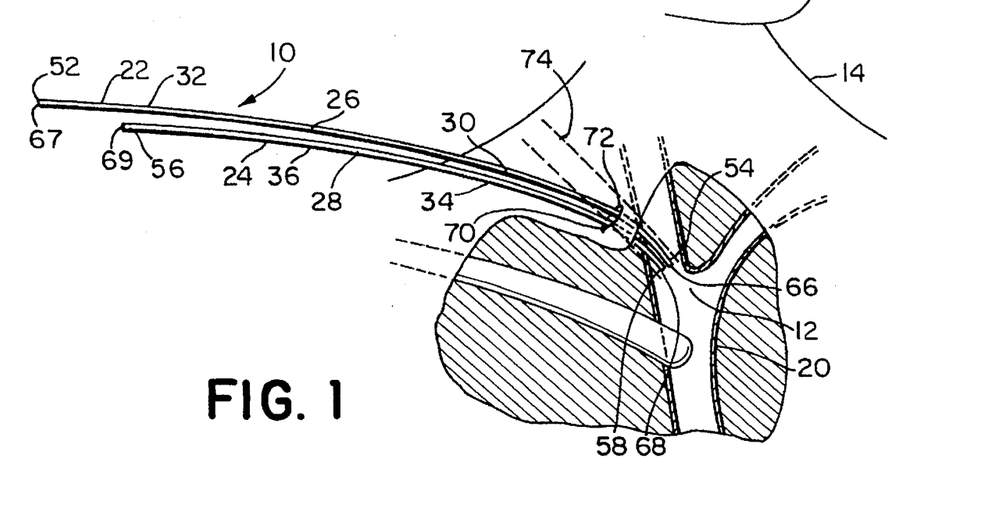
FIG. 1 is a partially broken-away diagrammatic view of a multiple catheter assembly being inserted into the internal jugular vein, in accordance with an embodiment of the present invention.
Figure 2:
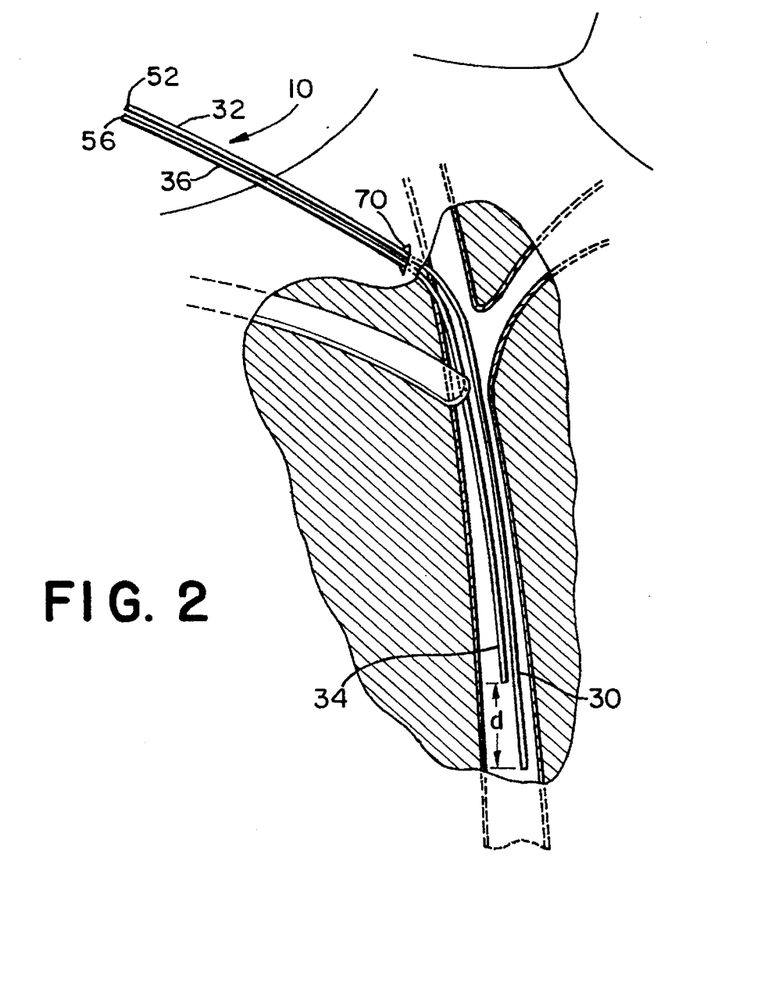
FIG. 2 is a partially broken-away diagrammatic view of the catheter assembly of FIG. 1 positioned within the internal jugular vein, after the proximal portions of the catheters are aligned.

Referring now to FIGS. 1 and 2, the multiple catheter assembly 10 includes at least a first single lumen catheter 22 having a lumen 26, and a second single lumen catheter 24 having a lumen 28. The lumens 26, 28 extend through the full length of their respective catheters. The lumens 26, 28 each have a generally circular cross section as viewed along a plane perpendicular to the longitudinal axis of the respective catheters. While the circular cross section is the preferred configuration for fluid flow in each lumen 26, 28, other configurations may be used without departing from the spirit of the present invention, such as, for example, oval, semi-circular, elliptical and kidney-bean shaped. In addition, the lumens 26, 28 may be of equal cross-sectional or of different cross-sectional areas (such as, for example, providing a smaller lumen for infusion of medication). The lumens 26, 28 shown in FIGS. 1–7 are of equal cross-sectional area. While two lumens of equal cross-sectional are shown in FIGS. 1–7, additional catheters (not shown) having lumens of the same or different cross sectional areas may also be included in a multiple catheter assembly for use in the present invention. For example, a multiple catheter assembly for hemodialysis may have two catheters with lumens of equal cross-sectional area for removal and return of blood and a third catheter having a third lumen of a smaller circular cross-section for infusion of medication. While the preferred catheter for the present method is a Tesio, as described above, other types of catheters may also be used in the present invention.

The first catheter 22 and the second catheter 24 are all preferably made of a biocompatible plastic or elastomer, more preferably from a biocompatible elastomer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the catheters 22, 24, it is most preferred that the polymeric material includes a polyurethane or a polyolefin polymeric material.

Suitable, preferred, biocompatible elastomers for use in forming the catheters 22, 24 include biocompatible elastomers such as medical grade silicone rubbers, polyvinyl chloride elastomers, polyolefin homopolymeric and copolymeric elastomers, urethane-based elastomers, and natural rubber or other synthetic rubbers. Preferably, the catheters 22, 24 are made of the elastomeric material such that the catheters 22, 24 are flexible, durable, soft, and easily conformable to the shape of the area to be catheterized 12 and/or the subcutaneous area 16. If the catheters 22, 24 are used for hemodialysis applications, they are preferably formed of a silicone elastomer which has a hardness of at least about 80-A on a Shore durometer scale. While it is preferred to have a higher Shore durometer hardness if a biocompatible elastomer is used, particularly for hemodialysis, it is also possible to make a device from an elastomer having a lower Shore durometer hardness without departing from the spirit of the invention. It will be understood, based on this disclosure, that the catheters 22, 24 may also be radiopaque depending on their intended use. A preferred Tesio catheter for use with the present method is available from MEDCOMP®, Harleysville, Pa.

The first catheter 22 is defined by a distal portion 30 and a proximal portion 32. Likewise, the second catheter 24 is defined by a distal portion 34 and a proximal portion 36. The distal catheter portions 30 and 34 are configured to be placed or inserted into, the area to be catheterized 12, whereas the proximal catheter portions 32, 36 remain outside of the area 12. Together, the proximal and distal portions of each catheter 22, 24 define the entire catheter length. In the embodiment of the invention shown in FIG. 6, the proximal catheter portions 32 and 36 may be secured to the surface 18 of the body 14 by a suitable fastening material 42 after the catheter assembly 10 is properly inserted in the area 12. This method of securing and positioning the catheter assembly 12 is typically used in emergency or acute procedures. In the embodiment shown in FIG. 3, the respective proximal catheter portions 32 and 36 may be independently secured in respective first and second subcutaneous tunnels 48, 50 in the subcutaneous area 16 of the body 14, in a manner known to those of ordinary skill in the art. Tunnelling may be used for either chronic or acute procedures.

Figure 4:
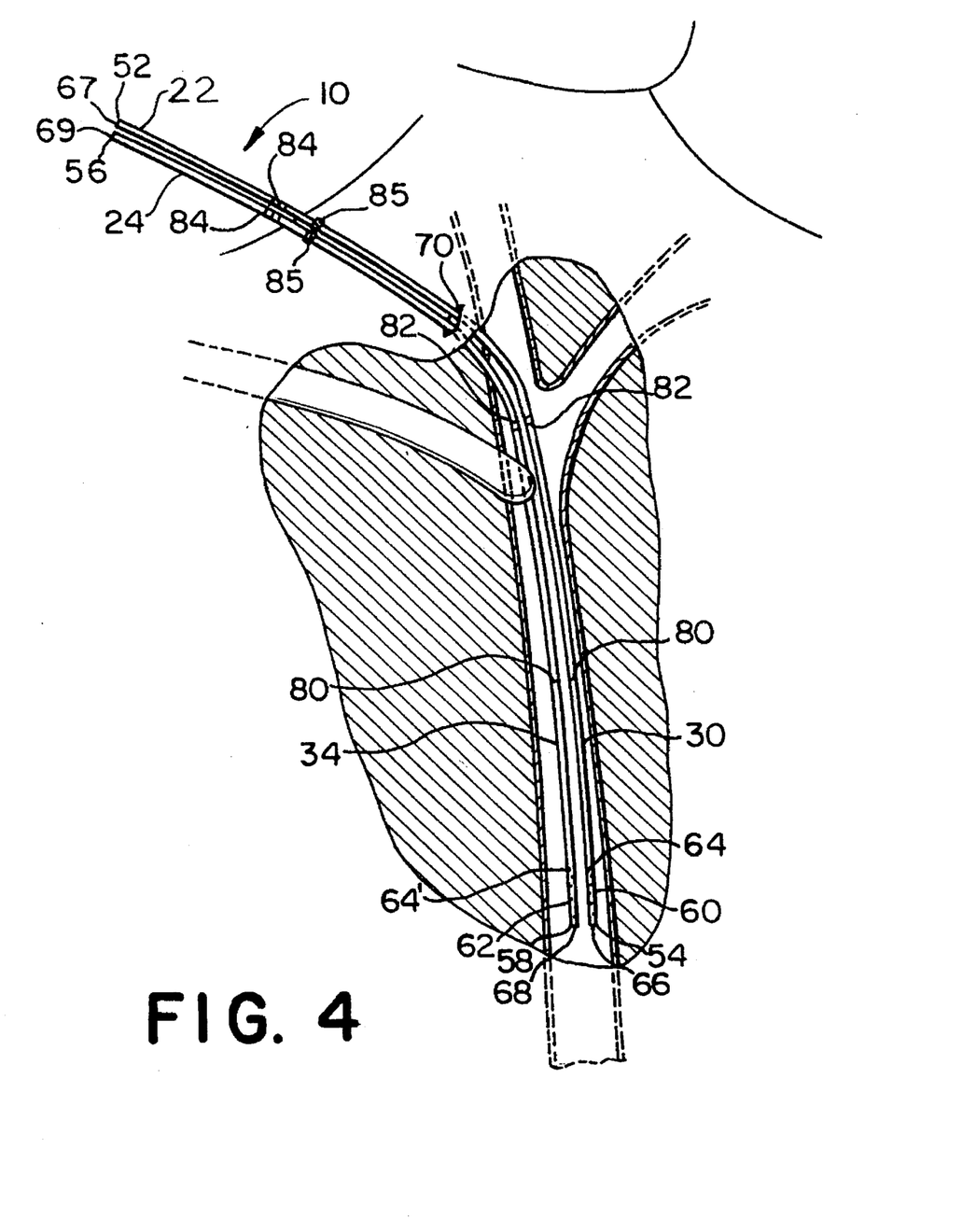
FIG. 4 is a partially broken-away diagrammatic view of a multiple catheter assembly after insertion into the internal jugular vein in accordance with an alternative embodiment of the present invention.
Figure 5:
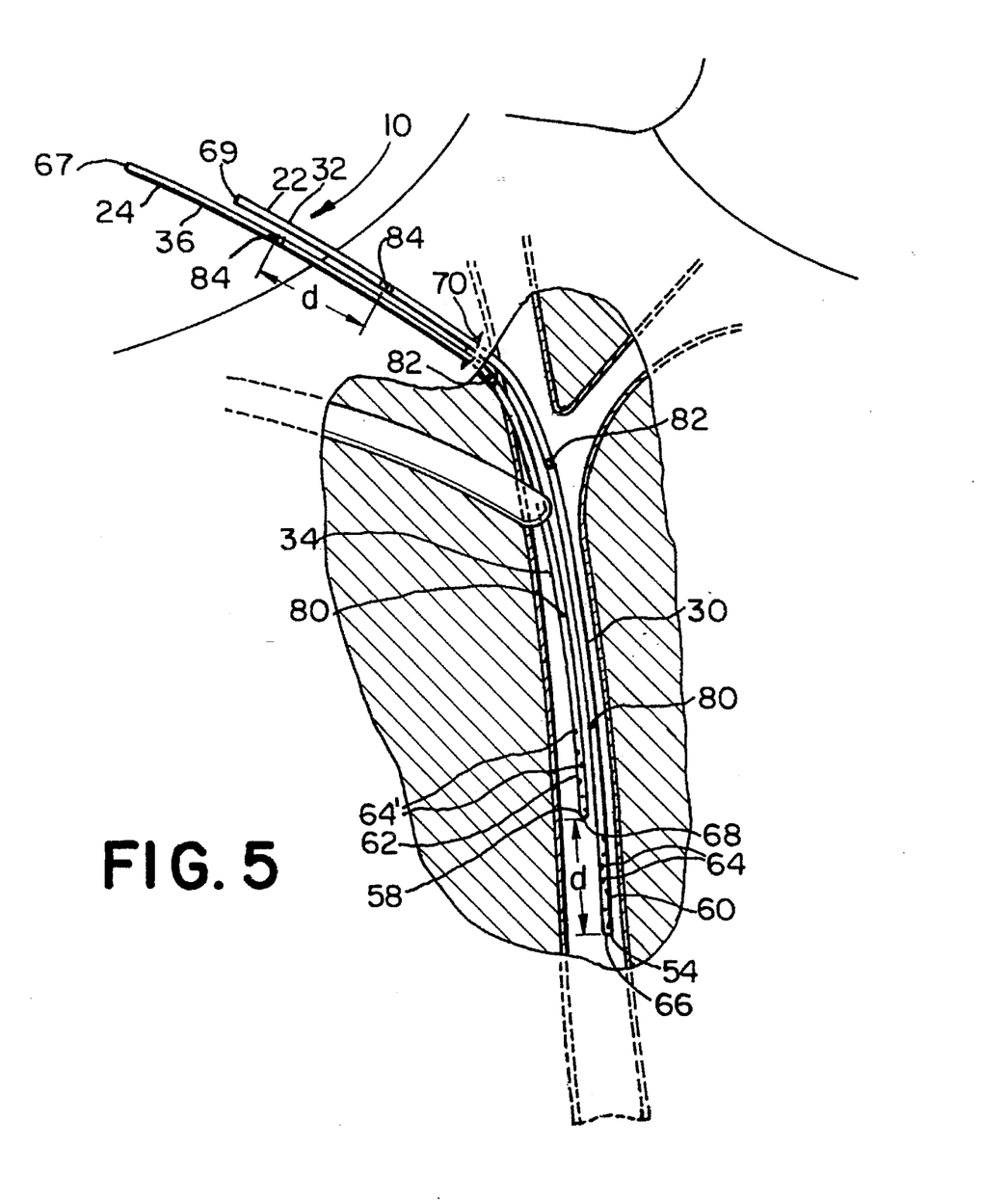
FIG. 5 is a partially broken-away diagrammatic view of the catheter assembly of FIG. 4 after adjusting the distance between the proximal portions of the catheters.
Figure 6:
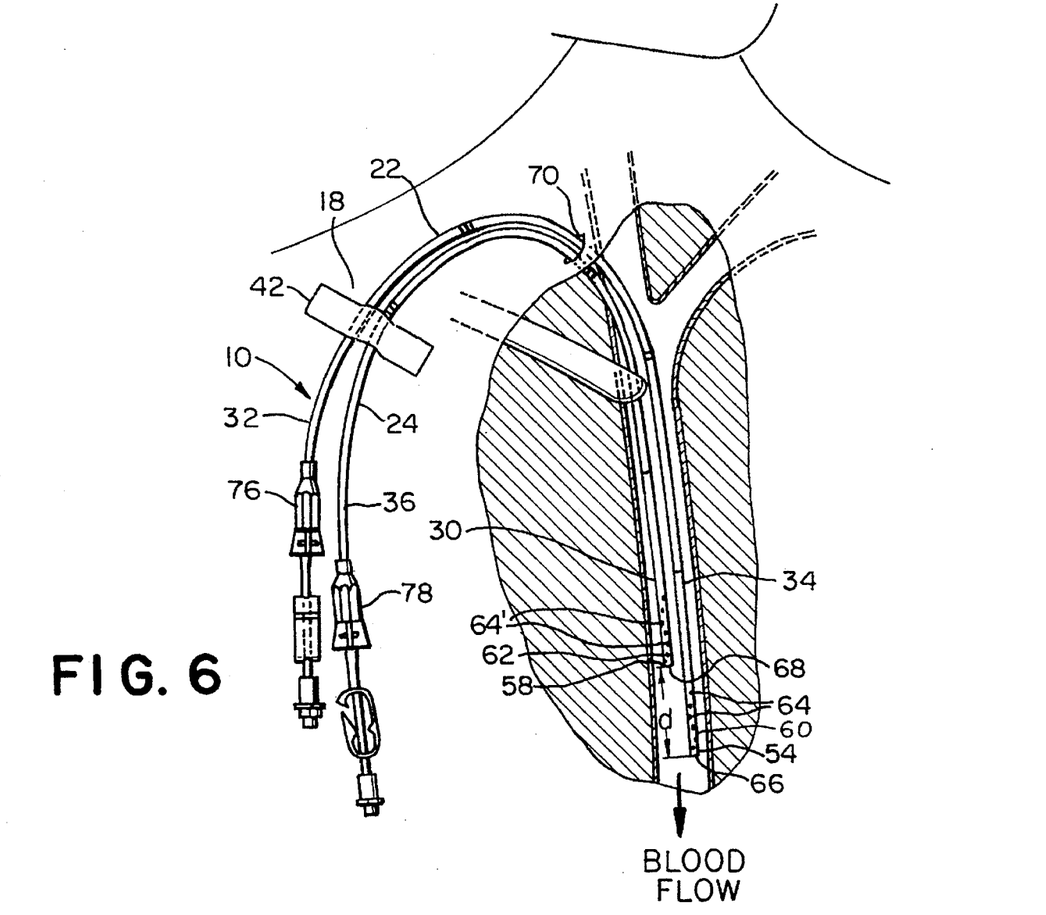
FIG. 6 is a partially broken-away diagrammatic view of the catheter assembly of FIG. 5 after externally securing the proximal portions of the catheters to the body.

In addition, the first catheter 22 has a proximal tip 52 at the furthest end of its proximal portion 32 and a distal tip 54 at the furthest end of its distal portion 30. Likewise, the second catheter 24 has a proximal tip 56 at the furthest end of its proximal portion 36 and a distal tip 58 at the furthest end of its distal portion 34. Furthermore, as best illustrated in FIGS. 4–6, the first catheter 22 is defined by a distal end region 60 near its distal tip 54. Likewise the second catheter 24 is defined by a distal end region 62 near its distal tip 58. The distal end regions 60 and 62 are provided with a plurality of apertures 64, 64'. The function of the apertures 64, 64' is described in more detail below. Since the lumen 26 preferably extends the entire longitudinal length of the first catheter 22, the first catheter 22 also has an opening 66 at its distal tip 54 and an opening 67 at its proximal tip 52. Likewise, since the lumen 28 preferably extends the entire longitudinal length of the second catheter 24, the second catheter 24 also has an opening 68 at its distal tip 58 and an opening 69 at its proximal tip 56. Of course, the openings 66 and 67 and are in fluid communication with each other, and the openings 68 and 69 are in fluid communication with each other.

The distal tips 54, 58 are preferably blunt in that they are configured to lie generally in a plane which is perpendicular to the longitudinal axis of each catheter 22, 24. The distal tips 54, 58 may alternatively be slightly rounded (not shown). The distal tips 54, 58 are preferably unitary with the catheter body as shown in the preferred embodiment such that the catheters are integrally molded. By configuring the distal tips 54, 58 in a blunt design and forming the entire catheter from a soft material such as a silicone elastomer, trauma to the area 12 and stenosis are minimized. It should be understood from this disclosure that while blunt tips are preferred, other tip configurations may be used in the present method, such as, for example, tapered ends for facilitating insertion or for accommodating other potential applications of the assembly 10. Such tapered designs are not preferred for hemodialysis applications of the assembly 10, as they may increase the risk of vessel wall trauma and stenosis.

Referring to FIGS. 1–7, each of the catheters 22, 24 is configured to have a suitable length and width useful for insertion into the internal jugular vein 20. When catheter insertion is completed, the distal tip 58 and end region 62 of the second catheter 24 is proximally and longitudinally spaced from the distal tip 54 and end region 60 of the first catheter 22 by a sufficient distance d (labeled in FIGS. 5 and 6) which substantially prevents recirculation of the purified blood and blood to be purified. The distance d, is preferably about 4 centimeters, however, it should be understood by one of ordinary skill in the art based on this disclosure, that d could be varied for different applications of the catheter assembly 10. Since blood flows toward the atrium, the blood flow in the internal jugular vein 20 is in a downward direction in the figures. Thus, the distal end region 60 and distal tip 54 of the first catheter 22 may be characterized as being "downstream" from the distal end region 62 and distal tip 58 of the second catheter 24.

During use of the multiple catheter assembly 10 for hemodialysis, blood is preferably drawn out of the internal jugular vein 20 through the opening 66 of the first catheter 22 (downstream catheter) and returned through the opening 68 of the second catheter 24 (upstream catheter). This flow direction is reversed from the conventional flow pattern of prior art catheters and provides higher flow rates, as discussed immediately below. However, it should be understood by one of ordinary skill in the art based on this disclosure that the direction of flow can be reversed, in the manner of conventional prior art multiple lumen catheter designs, such that blood is drawn from the upstream catheter and returned through the downstream catheter.

By using the downstream lumen for drawing blood, the blood to be purified may be safely and efficiently drawn from an area closer to the right atrium of the heart in which the blood has a higher flow rate. This (or the Tesio) catheter assembly 10 is designed to function efficiently with new and effectively higher flow rate dialysis devices which have flow rates of about 450 cc/min. The ability to use higher flow rates without collapse of the lumens, as in multiple lumen catheters, decreases the time necessary for a patient to undergo conventional dialysis treatments, a significant patient benefit.

Referring to FIGS. 5 and 6, the separation distance d is preferably about 4 centimeters. This separation distance d is longer than the traditional spacing of return and intake openings of multiple lumen catheters which is typically about 2 centimeters. The preferred longer distance d, in combination with the ability of the distal portions 30, 34 to move independently in the vein 20, helps to prevent recirculation of purified blood returned upstream through the lumen 28 with blood to be purified being drawn through the lumen 26.

As shown in FIGS. 4–6, it is preferred that the distal end regions 60 and 62 be provided with a plurality of apertures 64, 64' Further, providing apertures helically around the full circumference of the distal end regions 60 and 62 prevents sucking of the first and second catheters 22, 24 against the blood vessel, and minimizes vibratory movement of the distal end regions 60 and 62 by equalizing the disturbances of intake and outtake flow through the apertures 64, 64'. Minimizing the vibratory movement helps prevent stenosis. The apertures 64, 64' also provide alternative openings in the distal portions 30, 34 of the catheters 22, 24 such that if flow becomes blocked at an opening 66 or 68, dialysis can continue while a replacement catheter is being provided.

An important feature of the invention is that before, during and after insertion of the multiple catheter assembly into the area 12, the first and second catheters 22, 24 are independently movable with respect to each other, or unattached to each other, along their entire length. Since the first and second catheters 22, 24 are independently movable with respect to each other, or unattached to each other, along their entire length, each catheter 22, 24 is independently adjustable to provide any desired longitudinal displacement therebetween. Furthermore, removal and replacement of one catheter can be performed independently and without interfering with the placement and functioning of the other catheter. Removing and replacing one catheter is less traumatic than removing and replacing an entire catheter assembly. These advantages speed up the catheterization procedure if a catheter must be replaced for any reason.

In the method of the present invention, an incision 70 is initially made at an insertion site 72 near or proximate the area to be catheterized 12. If the catheter assembly 10 is used for hemodialysis and the area to be catheterized 12 is the internal jugular vein 20, the incision 70 is made in the clavicular triangle region, as shown for example, in FIGS. 1–6. The exact location of the insertion site 72 can be varied by the physician. In accordance with the Seldinger technique, a narrow needle is inserted through the incision 70 and into the vein 20. A guidewire is then passed through the needle and the needle is removed. In the Seldinger technique, the next step would be to advance a catheter over the guidewire. However, in the present invention, a dilator 74 (shown in phantom in FIG. 1) is introduced around the guidewire and partially into the vein 20. Once the dilator 74 is in place, the guidewire is removed and the distal portions 30, 34 of the first and second catheters 22, 24 are inserted into the dilator 74 in a juxtaposed manner, as shown in FIG. 1. The distal portions 30, 34 are inserted until they are properly positioned within the area 12, as shown in FIGS. 2 and 4. The dilator 74 is then removed, leaving the distal portions 30, 34 of the first and second catheters 22, 24 in the area 12. Each of the catheters 22, 24 may freely and independently move within the area 12.

Figure 3:
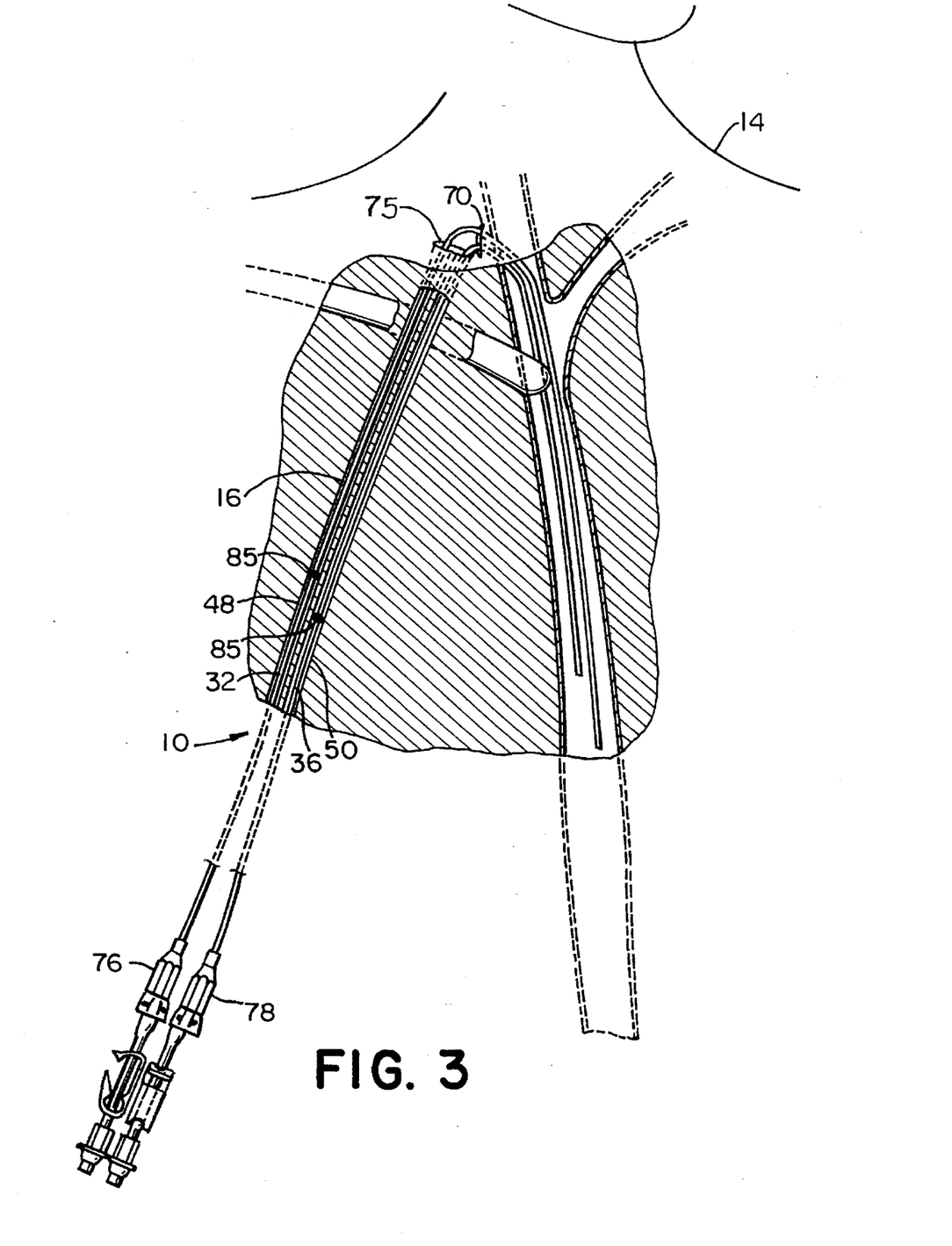
FIG. 3 is a partially broken-away diagrammatic view of the catheter assembly of FIG. 2 after the proximal portions of the catheters are subcutaneously secured.

The longitudinal distance between the proximal portions 32, 36 of the first and second catheters 22, 24 is adjusted then to provide a predetermined longitudinal distance d between the distal portions 30, 34 of the first and second catheters 22, 24 within the area 12, as shown in FIGS. 2 and 5. The incision 70 is closed and the proximal portions 32, 36 are secured to a fixed source or location in or on the body 14. As described above, the fixed source or location may be a subcutaneous area 16 in the body 14 (shown in FIG. 3) or an external surface 18 of the body 14 (shown in FIG. 6). If the catheters 22, 24 are externally secured, the incision is preferably closed before securing the proximal portions 32, 36, but may also be closed after securement. If the catheters 22, 24 are secured in the first and second subcutaneous tunnels 48, 50, the tunnelling procedure is performed through the incision 70, while the incision 70 is open. When the tunnelling procedure is completed, the incision 70 is closed. Alternatively, as shown in FIG. 3, the incision 70 is closed before the tunnelling procedure, and a second incision 75 is made to perform the tunnelling procedure. When the tunnelling procedure is completed, the second incision 75 is closed.

Once properly in place, the multiple catheter assembly 10 has many advantages. For example, since the first and second catheters 22 and 24 are independently movable with respect to each other, or unattached to each other, along their entire length, each catheter 22, 24 is independently adjustable to provide any desired longitudinal displacement therebetween. Furthermore, if one of the catheters becomes blocked or otherwise needs to be removed and replaced, the catheter may be removed and replaced without moving or displacing the other catheter. Accordingly, hemodialysis need not be stopped when a catheter needs replacement, thereby decreasing dialysis time and the need for unnecessary surgical procedures.

As shown in FIGS. 3 and 6, after the multiple catheter assembly 10 is in place, one end of a connector assembly 76 is attached to the proximal portion 32 of the first catheter 22, preferably at or near its proximal tip 52. Likewise, one end of a connector assembly 78 is attached to the proximal portion 36 of the second catheter 24, preferably at or near its proximal tip 56. The other ends of the connector assemblies 76, 78 are attached to respective fluid inlets and outlets of a hemodialysis unit, or other fluid transfer equipment (not shown). The connector assemblies 76, 78 have fluid passages therethrough. In this manner, the proximal portions 32, 36 of the first and second catheters 22, 24 are in fluid communication with the hemodialysis unit. The connector assemblies 76, 78 are described in more detail below with respect to FIG. 7.

FIGS. 1 and 2 illustrate one embodiment of the present method in which the longitudinal distance between the proximal portions 32, 36 of the first and second catheters 22, 24 is adjusted by aligning the proximal tips 52, 56. FIGS. 4 and 5 show an alternative embodiment in which the longitudinal distance between the proximal portion 32, 34 is adjusted to be shifted relative to each other by a longitudinal separation distance d.

Turning first to FIG. 1, the first catheter 22 is presized to have a first longitudinal length and the second catheter 24 is presized to have a second longitudinal length shorter than the first longitudinal length by the distance d (i.e., the first catheter 22 is longer than the second catheter 24 by the distance d). During the insertion step shown in FIG. 1, the distal tips 54, 58 are generally adjacent to each other when the distal portions 30, 34 are inserted into the dilator 74. After the dilator 74 is removed, the proximal portions 32, 36 are aligned so that the proximal tips 52, 56 are generally adjacent to each other, as shown in FIG. 2. That is, the longitudinal distance between the proximal tips 52, 56 is about zero. This causes the longitudinal distance between the distal portions 30 and 34 to become the distance d.

It should be appreciated that in the adjustment technique of FIGS. 1 and 2, it is not even necessary for the distal tips 54, 58 to be generally adjacent to each other when the distal portions 30, 34 are inserted into the dilator 74. It is only necessary that after insertion of the distal portions 30, 34, the proximal tips 52, 56 become generally aligned with each other.

Turning next to FIGS. 4 and 5, the first and second catheters 22 and 24 are identical in longitudinal length. One or both of the first and second catheters 22, 24 are provided with markings for use in adjusting the longitudinal distance between the proximal portions of the catheters 22, 24.

In the illustrated embodiment of the invention, the markings are longitudinally spaced bands on the external circumferential surface of the catheters 22, 24. The catheters 22, 24 have three sets of such markings imprinted thereon. For example, the first catheter 22 has a first marking 80 about ¼ of the distance from the distal tip 54 to proximal tip 52, a second marking 82 about ¼ of the distance from the proximal tip 52 to the distal tip 54, and a third marking 84 about midway between the distal tip 54 and the proximal tip 52. Each marking has a different number of bands to distinguish the markings from one another. In the illustrated embodiment of the invention, the first marking 80 has one band, the second marking 82 has two closely adjacent bands, and the third marking 84 has three closely adjacent bands. Prior art Tesio catheters include markings 80, 82 and 84, as described above and shown in the figures. However, heretofore, the markings were not used to adjust the relative longitudinal distance between two adjacent catheters inserted into a single incision. Instead, the markings were used to gauge how deep an individual Tesio catheter is inside a vessel.

Referring to FIG. 4, first and second catheters 22, 24 of equal length are inserted into the area 12 with the proximal tips B2, 56 generally aligned next to each other. Referring next to FIG. 5, the proximal portions 32, 36 are longitudinally adjusted relative to each other until a predetermined longitudinal distance d is achieved between the third markings 84 of the two catheters 22, 24. This adjustment creates a similar longitudinal separation distance d between the distal portions 30, 34 and tips 54, 58 of the two catheters 22, 24.

It should also be appreciated that the adjustment technique shown in FIGS. 4 and 5 could have been equally performed by merely adjusting the relative longitudinal distance between the proximal tips 52, 56 of the two catheters 22, 24 without use of markings 80, 82 or 84. It should further be appreciated that other types of markings may be used. The scope of the invention includes any marking which provides a means to adjust the relative longitudinal spacing between the two catheters 22, 24.

In the adjustment technique of FIGS. 1 and 2, the catheters 22, 24 are preformed in different lengths so that when the proximal tips 52, 56 are aligned, the appropriate distal separation distance d is achieved. In the adjustment technique of FIGS. 4 and 5, it is unnecessary to preform two different size catheters. One standard size catheter may be used for both the first and second catheters 22, 24. At least one marking provides a reference for creating the longitudinal separation distance d between the distal end regions 60, 62 and their respective distal tips 54, 58.

Once the multiple catheter assembly 10 is inserted and adjusted, and the incision is closed, the assembly 10 is secured. As generally described above, FIG. 6 shows a securing method which can be used for acute procedures. FIG. 3 shows an alternative securing method typically useful in either acute or chronic procedures.

Referring to FIG. 6, the catheters 22, 24 are secured to the external surface 18 of the body 14 by fastening material 42, such as adhesive tape. Referring to FIG. 3, respective proximal catheter portions 32, 36 are independently secured in respective first and second subcutaneous tunnels 48, 50 in the subcutaneous area 16 of the body 14 in a manner known to those of ordinary skill in the art. To further ensure that the proximal catheter portions 32, 36 remain secured in the subcutaneous area 16 of the body 14, one or more anchoring members, such as a tissue ingrowth cuff 85, are positioned around (i.e., circumferentially disposed on) proximal portions 32, 36, such that the members will be situated in the subcutaneous area 16 after tunnelling, as is well-known in the prior art.

Figure 7:
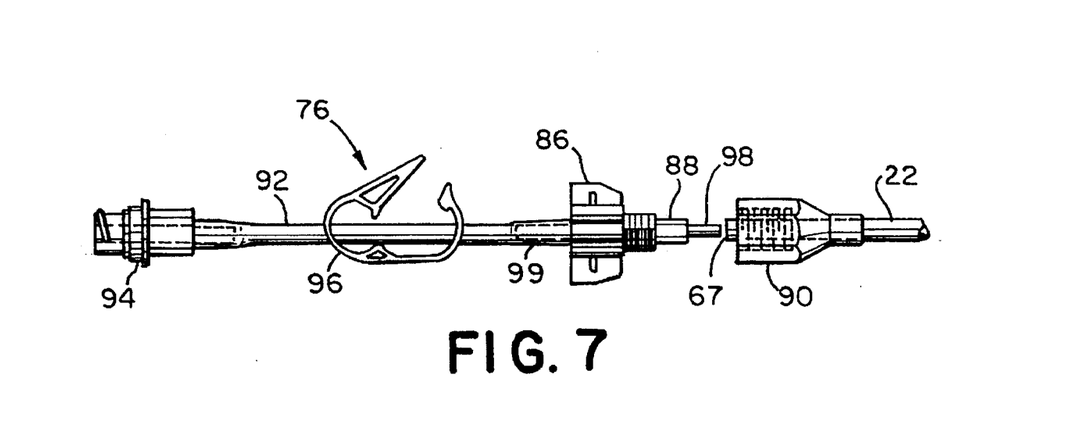
FIG. 7 is a partially exploded view of a connector assembly suitable for use with the multiple catheter assemblies of FIGS. 1 and 4.

FIG. 7 shows a partially exploded view of the connector assembly 76 (the connector assembly 76 being of identical construction) as it appears attached to the catheter 22. In use, the connector assembly 78 is preassembled and attached to the catheter 22 after it is inserted, adjusted and secured to the body 14.

The connector assembly 76 includes a hollow connection piece 86, compression ring 88, covering 90, flexible extension tube 92, female luer lock 94 and clamp 96. The connection piece 86 has a metal tube 98 extending from one end and a rigid tube 99 (shown in phantom), such as hard plastic, extending from the other end. The outer diameter of the metal tube 98 is sized to fit snugly inside the first catheter 22, whereas the outer diameter of the rigid tube 99 is sized to fit snugly inside one end of the extension tube 92. The female luer lock 94 fits snugly inside the other end of the extension tube 92. The clamp 96, which may be a squeeze lock clamp, is placed on the extension tube 92. In this manner, fluid flow through the catheter 22 may be controlled from a tube external to the catheter 22. In prior connector designs, fluid flow through a Tesio catheter was controlled by placing the clamp 96 directly on the catheter. The present connector is desirable because it decreases the risk of weakening the catheter, or of potentially causing breaks or leaks in the catheter.

The female luer lock 94 may be substituted by another type of quick connect fittings, ferrule connectors, threadable connector, and the like.

To attach the connector assembly 76 to the first catheter 22, the covering 90 is slipped onto the proximal portion 32 of the first catheter. The metal tube 98 of the connection piece 86 is then inserted into the opening 67 of the first catheter 22 and pushed a short distance into the catheter 22. This connecting region is protected by the covering 90 which is inserted over the compression ring 88 and screwed onto threads of the connection piece 86.

In the disclosed embodiment of the invention, the first and second catheters 22, 24 are unattached to each other along their entire length. However, to practice the present method, it is only necessary for the first and second catheters 22, 24 to be independently movable with respect to each other along their entire length. The first and second catheters 22, 24 may be attached to each other by material which allows one or both catheters 22, 24 to move longitudinally with respect to the other. For example, the proximal portions 32, 36 of the first and second catheters 22, 24 may be joined by a retaining sleeve (not shown) which fits loosely around one or both of the catheters 22, 24, and which allows one or both of the catheters 22, 24 to slip through the retaining sleeve.

In the disclosed embodiment, all incisions are closed before catheterization begins. If necessary, catheterization may be performed with an open incision, although the preferred technique is to close all incisions before catheterizing.

The present invention provides significant advantages over prior art methods of inserting Tesio catheters, including the ability to adjust the relative longitudinal distance between the two catheters, the ability to independently replace one catheter without removing the other catheter, and the ability to insert two catheters with one insertion procedure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for inserting a multiple catheter assembly into an area of a body to be catheterized, the assembly comprising a first and a second catheter, each catheter having a distal portion and a proximal portion, the first catheter for withdrawing fluid from the area and the second catheter for delivering fluid to the area, the first and second catheters being independently movable with respect to each other along their entire length, the method comprising the steps of:
   (a) making an incision near the area;
   (b) inserting the distal portions of the first and second catheters in juxtaposed relation through the incision and through a single insertion site into the area;
   (c) adjusting a longitudinal distance between the proximal portions of the first and second catheters to provide a predetermined longitudinal distance between the distal portions of the first and second catheters within the area; and
   (d) securing the proximal portions of the first and second catheters.

2. The method according to claim 1 wherein the proximal portions of the first and second catheters are in fluid communication with a hemodialysis unit.

3. The method according to claim 2 further comprising after step (d):
   (e) attaching removable connectors having fluid passages therethrough to the proximal portions of the first and second catheters.

4. The method according to claim 2 further comprising:
   (e) attaching removable connectors having fluid passages therethrough to the proximal portions of the first and second catheters, wherein each removable connector includes an extension tube having a clamp for controlling fluid flow through the connector.

5. The method according to claim 1 further comprising subcutaneously and independently securing the proximal portions of the first and second catheters.

6. The method according to claim 5 wherein the proximal portions of the first and second catheters are each subcutaneously secured by a tissue ingrowth cuff positioned around the proximal portions of the first and second catheters.

7. The method according to claim 5 wherein the proximal portions of the first and second catheters each include at least one circumferentially disposed anchoring member, the method further comprising the step of subcutaneously positioning the anchoring member in the body.

8. The method according to claim 1 further comprising, after step (a), inserting a dilator partially into the area.

9. The method according to claim 8 further comprising simultaneously inserting the first and second catheters into the dilator in a juxtaposed manner, and removing the dilator after the first and second catheters are positioned in the area.

10. The method according to claim 1 wherein the proximal portion of the first catheter has at least one marking, wherein step (c) includes using the marking for adjusting the longitudinal distance between the proximal portions of the first and second catheters.

11. The method according to claim 1 wherein the proximal portions of the first and second catheters each have at least one marking, wherein step (c) includes using a marking on each of the first and second catheters for adjusting the longitudinal distance between the proximal portions of the first and second catheters.

12. The method according to claim 1 wherein the proximal portions are secured by externally affixing the proximal portions to a patient's body.

13. The method according to claim 1 wherein the area is a blood vessel.

14. The method according to claim 1 wherein the first catheter has a first length, the second catheter has a second length shorter than the first length, the first and second catheters each includes a proximal tip, and proximal portions of the first and second catheters are adjusted by aligning the proximal tips of the first and second catheters such that the longitudinal distance between the tips of the first and second catheters is about zero.

15. The method according to claim 1 wherein the multiple catheter assembly is inserted into an internal jugular vein of a human being, near the right atrium of the heart, wherein step (c) includes adjusting the longitudinal distance between the proximal portions of the first and second catheters such that the distal portion of the first catheter is closer to the heart than the distal portion of the second catheter.

16. The method according to claim 1 further comprising after step (c):
   (e) closing the incision.

17. A method for inserting a multiple catheter assembly into an area of a body to be catheterized, the assembly comprising a first and a second catheter, each catheter having a distal portion and a proximal portion, the first catheter for withdrawing fluid from the area and the second catheter for delivering fluid to the area, the first and second catheters being unattached to each other along their entire length, the method comprising the steps of:
   (a) making an incision near the area;
   (b) inserting the distal portions of the first and second catheters in juxtaposed relation through the incision and through a single insertion site into the area;
   (c) adjusting a longitudinal distance between the proximal portions of the first and second catheters to provide a predetermined longitudinal distance between the distal portions of the first and second catheters within the area; and
   (d) securing the proximal portions of the first and second catheters.

18. The method according to claim 17 further comprising after step (c):
   (e) closing the incision.

19. In a method for inserting a multiple catheter assembly into an area of a body to be catheterized, the assembly comprising a first and a second catheter, each catheter having a distal portion and a proximal portion, the first catheter for withdrawing fluid from the area and the second catheter for delivering fluid to the area, the first and second catheters being unattached to each other along their entire length, the improvement comprising the steps of:
   (a) inserting the distal portions of the first and second catheters in juxtaposed relation into the area through a single incision made near the area to be catheterized and through a single insertion site into the vessel;
   (b) adjusting a longitudinal distance between the proximal portions of the first and second catheters to provide a predetermined longitudinal distance between the distal portions of the first and second catheters within the area; and
   (c) securing the proximal portions of the first and second catheters.

20. The method according to claim 19 further comprising after step (b):
   (d) closing the incision.

* * * * *